United States Patent
Seong et al.

(10) Patent No.: US 7,390,900 B2
(45) Date of Patent: Jun. 24, 2008

(54) SILANE COUPLING AGENT AND METHOD FOR MANUFACTURING THE SAME

(75) Inventors: Hye-ran Seong, Seoul (KR); Se-ra Kim, Daejeon (KR); In-cheon Han, Seoul (KR); Suk-ky Chang, Daejeon (KR)

(73) Assignee: LG Chem. Ltd., Seoul (KR)

( * ) Notice: Subject to any disclaimer, the term of this patent is extended or adjusted under 35 U.S.C. 154(b) by 576 days.

(21) Appl. No.: 11/141,013

(22) Filed: Jun. 1, 2005

(65) Prior Publication Data

US 2005/0277774 A1     Dec. 15, 2005

(30) Foreign Application Priority Data

Jun. 15, 2004     (KR)     ............... 10-2004-0044151

(51) Int. Cl.
*C07F 7/02*     (2006.01)
(52) U.S. Cl. ....................................... 546/14
(58) Field of Classification Search ............... 546/14
See application file for complete search history.

(56) References Cited

FOREIGN PATENT DOCUMENTS

JP     10-067787     3/1998
JP     11-335378     12/1999

*Primary Examiner*—Zinna N Davis
(74) *Attorney, Agent, or Firm*—McKenna Long & Aldridge LLP

(57) ABSTRACT

The present invention relates to a novel silane coupling agent represented by Formula 1 below and a method for manufacturing the same. Because the compound has urethane and pyridine functional groups, it has superior storage stability and good adhesion property to a matrix resin having hydroxy groups, and thus can be used in a variety of applications.

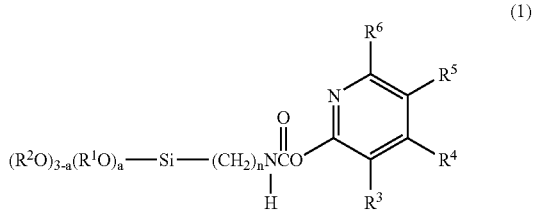

(1)

where each of $R^1$ and $R^2$ is hydrogen or $C_1$-$C_3$ alkyl, a is an integer from 0 to 3, each of $R^3$, $R^4$, $R^5$ and $R^6$ is hydrogen, $C_1$-$C_{10}$ alkyl, halogen, trifluoroalkyl or alkoxyalkyl and n is an integer from 1 to 3.

8 Claims, No Drawings

SILANE COUPLING AGENT AND METHOD FOR MANUFACTURING THE SAME

CROSS-REFERENCE TO RELATED APPLICATIONS

This application claims the benefit of Korean Patent Application No. 10-2004-0044151, filed Jun. 15, 2004 in Korea, which is hereby incorporated by reference in its entirety.

TECHNICAL FIELD

The present invention relates to a novel silane coupling agent and a method for manufacturing the same. More particularly, the present invention relates to a novel silane coupling agent having urethane and pyridine functional groups, thus having superior storage stability, and being useful in enhancing affinity of an organic resin with an inorganic filler and improving adhesion property of a matrix resin type coating layer to a substrate and a method for manufacturing the same.

BACKGROUND ART

Because the silane coupling agent has two or more different functional groups in one molecule, it is commonly used as medium for interconnecting organic and inorganic materials, which are otherwise hard to be combined. One of the functional groups, which may be methoxy or ethoxy, binds with inorganic materials such as glass, metal, sand, etc. The other functional group, which may be vinyl, epoxy, amino, methacryl or mercapto, reacts with organic materials such as a variety of synthetic resins. With regard to these properties, a variety of silane coupling agents are used to enhance affinity of organic resins with inorganic fillers or improve adhesion property of matrix resin type coating layers to substrates. For a silane coupling agent to be able to satisfy such needs, there should be chemical bonding or physical interactions between the functional group of an organic resin and the organic functional group of the silane coupling agent. In addition, there should be chemical bonding between the alkoxysilyl group of the silane coupling agent and an inorganic filler or a substrate. Accordingly, a variety of silane coupling agents having different organic functional groups are currently used.

At present, silane coupling agents containing urethane groups are widely used. Japanese Patent Publication No. Hei 10-67787 discloses a method of manufacturing a silane coupling agent by thermal treatment of isocyanate silane and diethanolamine. Japanese Patent Publication No. Hei 11-335378 discloses a method of manufacturing a silane coupling agent by reacting aminosilane with vinylbenzyl chloride and isocyanate. However, silane coupling agents having organic functional groups such as suitable for the case in which hydroxy groups (—OH) are present in the matrix resin are insufficient, as yet.

It is an object of the present invention to provide novel, useful silane coupling agent capable of binding with a matrix having hydroxy groups and a method for manufacturing the same.

DISCLOSURE

To attain the object, the present invention provides a silane coupling agent represented by Formula 1 below:

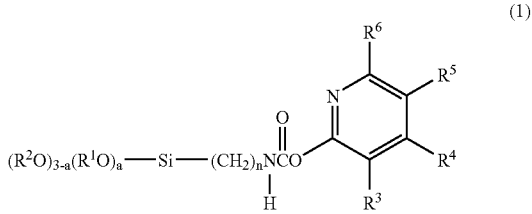

where each of $R^1$ and $R^2$ is hydrogen or $C_1$-$C_3$ alkyl, a is an integer from 0 to 3, each of $R^3$, $R^4$, $R^5$ and $R^6$ is selected from the group consisting of hydrogen, $C_1$-$C_{10}$ alkyl, halogen, trifluoroalkyl and alkoxyalkyl and n is an integer from 1 to 3.

The present invention also provides a method of manufacturing the silane coupling agent represented by Formula 1, which is characterized by reacting isocyanate and pyridinol in a reaction solvent at room temperature in the presence of a catalyst.

The isocyanate may be selected from the group consisting of 1-trimethoxysilylmethyl isocyanate, 2-trimethoxysilylethyl isocyanate, 3-trimethoxysilylpropyl isocyanate, 1-triethoxysilylmethyl isocyanate, 2triethoxysilylethyl isocyanate and 3-triethoxysilylpropyl isocyanate.

The pyridinol may be selected from the group consisting of 2-hydroxypyridine, 5-chloro-2-pyridinol, 4-methyl-2-pyridinol, 5-trifluoromethyl-2-pyridinol and 4-methoxymethyl-2-pyridinol.

The catalyst may be selected from the group consisting of lead stannate, dibutyltin dilaurate, dibutyltin maleate, dibutyltin diacetate, dibutyltin dilauryl mercaptide and dimethyltin dichloride.

The reaction solvent may be selected from the group consisting of a halogenated alkyl solvent, a cyclic ether solvent and an aromatic organic solvent.

The halogenated alkyl solvent may be selected from the group consisting of chloroform, methylene chloride and dichloroethane. The cyclic ether solvent may be tetrahydrofuran or dioxin. And, the aromatic organic solvent may be selected from the group consisting of benzene, toluene and xylene.

The molar ratio of the isocyanate to the pyridinol may be 1:1.

Hereunder is given a more detailed description of the present invention.

According to the present invention, urethane and pyridine groups, which have good binding ability to hydroxy groups, are introduced into the silane coupling agent in order to improve adhesion property to a matrix resin having hydroxy groups.

The silane coupling agent according to the present invention has two kinds of reacting functional groups. One forms chemical bonding with an organic material, and the other forms chemical bonding with an inorganic material. For example, the trialkoxysilyl group reacts with silanol, which is present on the surface of inorganic material such as silicate, to form a chemical bonding. Also, depending on the functional groups present in the matrix resin to be bound, several organic functional groups may be introduced into the silane coupling agent. Here, designing an adequate organic group to be introduced into the silane coupling agent may be the key to form a selective chemical bonding to the specific functional group of the resin.

Isocyanate is reacted with pyridinol in order to introduce a urethane group to the silane coupling agent, the target compound. When organometallic catalyst such as dibutyltin dilaurate is used, the target compound may be obtained at room temperature with good production yield within 2-3 hours. Without catalyst, the reaction hardly proceeds at room temperature and byproducts tend to be generated at an elevated temperature.

The isocyanate may be 1-trimethoxysilylmethyl isocyanate, 2-trimethoxysilylethyl isocyanate, 3-trimethoxysilylpropyl isocyanate, 1-triethoxysilylmethyl isocyanate, 2-triethoxysilylethyl isocyanate, 3-triethoxysilylpropyl isocyanate, etc.

The pyridinol, the other reactant, may be 2-hydroxypyridine, 5-chloro-2-pyridinol, 4-methyl-2-pyridinol, 5-trifluoromethyl-2-pyridinol, 4-methoxymethyl-2-pyridinol, etc.

Preferably, the isocyanate and the pyridinol are reacted at a molar ratio of 1:1. Using equimolar reactants, waste of starting materials can be reduced.

In the reaction of the isocyanate and the pyridinol, lead stannate, dibutyltin dilaurate, dibutyltin maleate, dibutyltin diacetate, dibutyltin dilauryl mercaptide, dimethyltin dichloride, etc. may be used as catalyst.

The reaction may be performed in a halogenated alkyl solvent such as chloroform, methylene chloride and dichloroethane; a cyclic ether solvent such as tetrahydrofuran and dioxin; or an aromatic organic solvent such as benzene, toluene and xylene.

In order to evaluate the resultant silane coupling agent's usefulness as a silane coupling agent by reacting with hydroxyl groups of a matrix resin, the following test is performed. In order to evaluate the effectiveness of the silane coupling agent as adhesion-promoting additive for improving adhesion property to a substrate, a matrix resin having hydroxy groups is synthesized and its adhesion property to glass is examined.

The acrylic resin used in the present invention is obtained from copolymerization of a (meth)acrylate ester monomer having a $C_1$-$C_{12}$ alkyl group and a vinylic monomer having a hydroxy group. The (meth)acrylate ester monomer having a $C_1$-$C_{12}$ alkyl group may be butyl (meth)acrylate, 2-ethylhexyl (meth)acrylate, ethyl (meth)acrylate, methyl (meth)acrylate, n-propyl (meth)acrylate, isopropyl (meth)acrylate, t-butyl (meth)acrylate, pentyl (meth)acrylate, n-octyl (meth)acrylate, isooctyl (meth)acrylate, isononyl (meth)acrylate, etc. These monomers may be used alone or in admixture. The vinylic monomer having a hydroxy group may be 2-hydroxyethyl (meth)acrylate, 2-hydroxypropyl (meth)acrylate, 2-hydroxyethylene glycol (meth)acrylate, 2-hydroxypropylene glycol (meth)acrylate, etc.

A crosslinking agent is added to the matrix resin having hydroxy groups, along with the silane coupling agent, in order to measure the change of adhesion property due to the silane coupling agent. The crosslinking agent may be tolylene diisocyanate, diphenylmethane diisocyanate, hexamethylene diisocyanate, a trimethylolpropane adduct of tolylene diisocyanate, etc.

Depending on needs, a plasticizer, an acrylic oligomer, an emulsifier, a birefringent low molecular weight compound, an epoxy resin, a hardener, a UV stabilizer, an antioxidant, a colorant, a modifier, a filler, etc. may be added to the acrylic resin.

Because the urethane and pyridine functional groups present in the silane coupling agent according to the present invention has good binding ability to the matrix having hydroxy groups, the silane coupling agent can enhance affinity to an inorganic filler and improve adhesion property to a substrate, when used as an additive.

BEST MODE

Hereinafter, the present invention is described in more detail through examples. However, the following examples are only for the understanding of the present invention and the present invention is not limited to or by the examples.

EXAMPLE 1

Synthesis of Silane Coupling Agent A 9.5 g of 2-hydroxypyridine was dissolved in 200 mL of THF. 24.7 g of 3-triethoxysilylpropyl isocyanate and 0.6 g of dibutyltin dilaurate were added. Reaction was performed for 2 hours while stirring at room temperature and under nitrogen atmosphere.

After the reaction was completed, the solvent was removed under reduced pressure. The product was dried in vacuum. 32.5 g of silane coupling agent A represented by Formula 2 below was obtained. The yield was 95%.

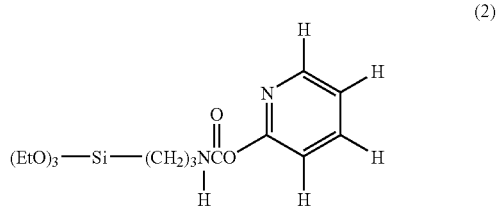

The resultant compound was colorless liquid. NMR analysis result was as follows.

$^1$H NMR (CDCl$_3$, 300 MHz): 0.72 (t, 2H), 1.24 (t, 9H), 1.76 (m, 2H), 3.43 (m, 2H), 3.83 (q, 6H), 6.34 (t, 1H), 6.60 (d, 1H), 7.42 (m, 1H), 8.43 (m, 1H), 10.64 (s, 1H).

$^{13}$C NMR (CDCl$_3$, 300 MHz): 2.50, 12.97, 17.56, 38.22, 53.10, 101.61, 117.28, 126.92, 135.93, 147.23, 159.87.

EXAMPLE 2

Synthesis of Silane Coupling Agent B 13 g of 5-chloro-2-pyridinol was dissolved in 200 mL of THF. 24.7 g of 3-triethoxysilylpropyl isocyanate and 0.6 g of dibutyltin dilaurate were added. Reaction was performed for 2 hours while stirring at room temperature and under nitrogen atmosphere.

After the reaction was completed, the solvent was removed under reduced pressure. The product was dried in vacuum. 33 g of silane coupling agent B represented by Formula 3 below was obtained. The yield was 88%.

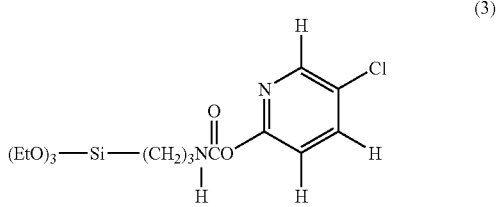

The resultant compound was colorless liquid. NMR analysis result was as follows.

$^1$H NMR (CDCl$_3$, 300 MHz): 0.72 (t, 2H), 1.24 (t, 9H), 1.76 (m, 2H), 3.43 (m, 2H), 3.83 (q, 6H), 6.45 (d, 1H), 7.51 (d, 1H), 7.67 (s, 1H), 10.64 (s, 1H).

$^{13}$C NMR (CDCl$_3$, 300 MHz): 2.50, 12.97, 17.56, 38.22, 53.10, 112.11, 119.74, 136.81, 147.23, 159.87, 161.05.

EXAMPLE 3

Synthesis of Silane Coupling Agent C 11 g of 5-trifluoromethyl-2-pyridinol was dissolved in 200 mL of THF. 24.7 g of 3-triethoxysilylpropyl isocyanate and 0.6 g of dibutyltin dilaurate were added. Reaction was performed for 2 hours while stirring at room temperature and under nitrogen atmosphere.

After the reaction was completed, the solvent was removed under reduced pressure. The product was dried in vacuum. 33 g of silane coupling agent C represented by Formula 4 below was obtained. The yield was 92%.

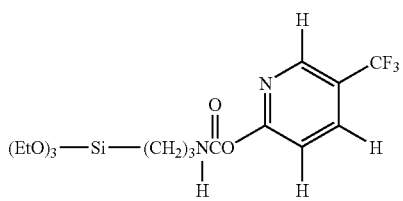

(4)

The resultant compound was colorless liquid. NMR analysis result was as follows.

$^1$H NMR (CDCl$_3$, 300 MHz): 0.72 (t, 2H), 1.24 (t, 9H) 1.76 (m, 2H), 3.43 (m, 2H), 3.83 (q, 6H), 6.45 (t, 1H), 6.72 (d, 1H), 8.39 (m, 1H), 10.64 (s, 1H).

$^{13}$C NMR (CDCl$_3$, 300 MHz): 2.50, 12.97, 17.56, 38.22, 42.55, 53.10, 101.43, 116.28, 126.67, 135.13, 145.11, 159.87.

EXAMPLE 4

Synthesis of Silane Coupling Agent D 10.9 g of 4-methyl-2-pyridinol was dissolved in 200 mL of THF. 24.7 g of 3-triethoxysilylpropyl isocyanate and 0.6 g of dibutyltin dilaurate were added. Reaction was performed for 2 hours while stirring at room temperature and under nitrogen atmosphere.

After the reaction was completed, the solvent was removed under reduced pressure. The product was dried in vacuum. 33 g of silane coupling agent D represented by Formula 5 below was obtained. The yield was 93%.

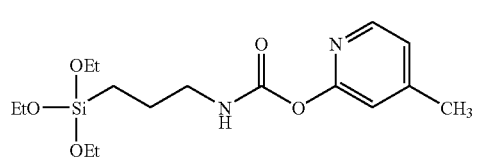

(5)

The resultant compound was colorless liquid. NMR analysis result was as follows.

$^1$H NMR (CDCl$_3$, 300 MHz): 0.72 (t, 2H), 1.24 (t, 9H), 1.76 (m, 2H), 2.45 (s, 3H), 3.43 (m, 2H), 3.83 (q, 6H), 6.45 (t, 1H), 7.42 (d, 1H), 8.43 (m, 1H), 10.64 (s, 1H).

$^{13}$C NMR (CDCl$_3$, 300 MHz): 2.50, 12.97, 17.56, 20.05, 38.22, 53.10, 101.64, 117.27, 126.87, 135.33, 147.11, 159.87.

EXAMPLE 5

Synthesis of Silane Coupling Agent E 12.5 g of 4-methoxy-2-pyridinol was dissolved in 200 mL of THF. 24.7 g of 3-triethoxysilylpropyl isocyanate and 0.6 g of dibutyltin dilaurate were added. Reaction was performed for 2 hours while stirring at room temperature and under nitrogen atmosphere.

After the reaction was completed, the solvent was removed under reduced pressure. The product was dried in vacuum. 34 g of silane coupling agent E represented by Formula 6 below was obtained. The yield was 91%.

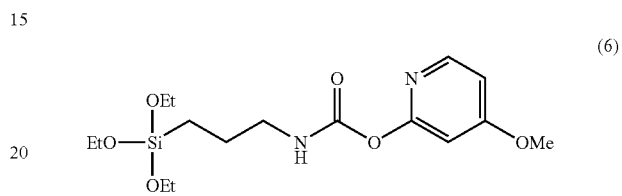

(6)

The resultant compound was colorless liquid. NMR analysis result was as follows.

$^1$H NMR (CDCl$_3$, 300 MHz): 0.72 (t, 2H), 1.24 (t, 9H) 1.76 (m, 2H), 3.43 (m, 2H), 3.59 (s, 3H), 3.83 (q, 6H), 6.45 (t, 1H), 7.42 (d, 1H), 8.43 (m, 1H), 10.64 (s, 1H).

$^{13}$C NMR (CDCl$_3$, 300 MHz): 2.50, 12.97, 17.56, 38.22, 53.10, 55.21, 101.64, 117.27, 126.87, 135.33, 147.11, 160.82.

EXAMPLE 6

Preparation of Acrylic Copolymer

To a 1000 CC reactor equipped with nitrogen gas reflux and an easily temperature-controlled cooler was added a monomer mixture comprising 98 parts by weight of n-ethyl acrylate (EA) and 2 parts by weight of 2-hydroxyethyl methacrylate (2-HEMA). 230 parts by weight of ethyl acetate (EAc) was added as solvent. Purging was performed with nitrogen gas for 20 minutes in order to remove oxygen. The temperature was maintained at 70° C. After homogenizing the mixture, 0.03 part by weight of azobisisobutyronitrile (AIBN) diluted to 50% in ethyl acetate was added as reaction initiator. Reaction was performed for 7 hours to obtain an acrylic copolymer having a molecular weight (measured using a polystyrene standard sample) of 900,000.

Preparation of Acrylic Resin Composition for Adhesion Property Test

To 100 parts by weight of the resultant acrylic copolymer were added 1.5 part by weight of a tolylene diisocyanate adduct of trimethylolpropane (TDI-1), as polyfunctinal isocyanate crosslinking agent, and 0.1 part by weight of silane coupling agent A synthesized in Example 1. The composition was diluted to an adequate concentration, mixed homogeneously and coated in between glass and PET film using a press roller.

EXAMPLE 7

The procedure of Example 6 was performed, except that silane coupling agent B synthesized in Example 2 was used instead of silane coupling agent A.

EXAMPLE 8

The procedure of Example 6 was performed, except that silane coupling agent C synthesized in Example 3 was used instead of silane coupling agent A.

EXAMPLE 9

The procedure of Example 6 was performed, except that silane coupling agent D synthesized in Example 4 was used instead of silane coupling agent A.

EXAMPLE 10

The procedure of Example 6 was performed, except that silane coupling agent E synthesized in Example 5 was used instead of silane coupling agent A.

COMPARATIVE EXAMPLE 1

The procedure of Example 6 was performed, except that silane coupling agent was not added.

COMPARATIVE EXAMPLE 2

The procedure of Example 6 was performed, except that ethyl-3-(triethoxysilyl)propyl carbamate was used instead of silane coupling agent A.

COMPARATIVE EXAMPLE 3

The procedure of Example 6 was performed, except that 2-(dimethylamino)ethyl-3-(triethoxysilyl)propyl carbamate was used instead of silane coupling agent A.

TESTING EXAMPLE

Adhesion property of the acrylic resin compositions prepared in Examples 6-10 and Comparative Examples to glass was evaluated as follows. The result is given in Table 1 below.

Adhesion Strength to Glass (180° Peeling Strength)

Glass plates coated with the acrylic resins prepared in Examples 6-10 and Comparative Examples were kept at room temperature for 1 hour. Then, they were kept under a dry condition of 60° C. and a wet condition of 60° C. and 90% R.H. for 10 hours. After keeping at room temperature again for 2 hours, adhesion strength to glass was measured with a tensile strength tester at a speed of 300 mm/min and with an angle of 180°.

TABLE 1

| Category | Adhesion strength to glass (g/25 mm) | |
|---|---|---|
|  | Dry condition | Wet condition |
| Example 6 | 490 | 680 |
| Example 7 | 400 | 550 |
| Example 8 | 450 | 630 |
| Example 9 | 470 | 610 |
| Example 10 | 460 | 600 |
| Comparative Example 1 | 110 | 90 |
| Comparative Example 2 | 115 | 200 |
| Comparative Example 3 | 120 | 250 |

As shown in Table 1, the acrylic resin compositions of Examples 6-10, in which the silane coupling agent according to the present invention was added, showed much superior adhesion property to glass to that of Comparative Example 1, in which no silane coupling agent was added, and those of Comparative Examples 2 and 3, in which the silane coupling agent having urethane group only was added.

INDUSTRIAL APPLICABILITY

As apparent from above description, the urethane and pyridine groups present in the compound according to the present invention enhances adhesion property to a matrix resin having hydroxy groups. Accordingly, the silane coupling agent according to the present invention can be used in various applications to improve storage stability, enhance affinity of organic resins to inorganic fillers or improve adhesion property of coating layers made of matrix resins to substrates.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A silane coupling agent comprising: a compound represented by Formula 1 below $$(R^2O)_{3-a}(R^1O)_a-Si-(CH_2)_n-\underset{H}{N}-\underset{\parallel}{C}-O-\text{pyridyl}(R^3,R^4,R^5,R^6) \quad (1)$$

where each of $R^1$ and $R^2$ is hydrogen or $C_1$-$C_3$ alkyl, a is an integer from 0 to 3, each of $R^3$, $R^4$, $R^5$ and $R^6$ is selected from the group consisting of hydrogen, $C_1$-$C_{10}$ alkyl, halogen, trifluoroalkyl and alkoxyalkyl and n is an integer from 1 to 3.

2. A method of preparing a silane coupling agent represented by Formula 1 below $$(R^2O)_{3-a}(R^1O)_a-Si-(CH_2)_n-\underset{H}{N}-\underset{\parallel}{C}-O-\text{pyridyl}(R^3,R^4,R^5,R^6) \quad (1)$$

where each of $R^1$ and $R^2$ is hydrogen or $C_1$-$C_3$ alkyl, a is an integer from 0 to 3, each of $R^3$, $R^4$, $R^5$ and $R^6$ is selected from the group consisting of hydrogen, $C_1$-$C_{10}$ alkyl, halogen, trifluoroalkyl and alkoxyalkyl and n is an integer from 1 to 3 comprising:

reacting isocyanate and pyridinol at room temperature in a reaction solvent in the presence of a catalyst.

3. The method of claim 2, wherein the isocyanate is selected from the group consisting of 1-trimethoxysilylmethyl isocyanate, 2-trimethoxysilylethyl isocyanate, 3-trimethoxysilylpropyl isocyanate, 1-triethoxysilylmethyl isocyanate, 2-triethoxysilylethyl isocyanate and 3-triethoxysilylpropyl isocyanate.

4. The method of claim 2, wherein the pyridinol is selected from the group consisting of 2-hydroxypyridine, 5-chloro-2-pyridinol, 4-methyl-2-pyridinol, 5-trifluoromethyl-2-pyridinol and 4-methoxymethyl-2-pyridinol.

5. The method of claim 2, wherein the catalyst is selected from the group consisting of lead stannate, dibutyltin dilaurate, dibutyltin maleate, dibutyltin diacetate, dibutyltin dilauryl mercaptide and dimethyltin dichloride.

6. The method of claim 2, wherein the reaction solvent is selected from the group consisting of a halogenated alkyl solvent, a cyclic ether solvent and an aromatic organic solvent.

7. The method of claim 6, wherein the halogenated alkyl solvent is selected from the group consisting of chloroform, methylene chloride and dichloroethane; the cyclic ether solvent is tetrahydrofuran or dioxin; and the aromatic organic solvent is selected from the group consisting of benzene, toluene and xylene.

8. The method of claim 2, wherein the molar ratio of the isocyanate to the pyridinol is 1:1.

* * * * *